(12) United States Patent
Ishida et al.

(10) Patent No.: US 8,433,095 B2
(45) Date of Patent: Apr. 30, 2013

(54) DROWSINESS DETECTOR

(75) Inventors: Kenji Ishida, Nagoya (JP); Satori Hachisuka, Nagoya (JP)

(73) Assignee: Denso Corporation, Kariya (JP)

( * ) Notice: Subject to any disclaimer, the term of this patent is extended or adjusted under 35 U.S.C. 154(b) by 534 days.

(21) Appl. No.: 12/654,976

(22) Filed: Jan. 12, 2010

(65) Prior Publication Data
US 2010/0202658 A1    Aug. 12, 2010

(30) Foreign Application Priority Data
Feb. 9, 2009    (JP) .................................. 2009-27186

(51) Int. Cl.
*G06K 9/00*    (2006.01)
(52) U.S. Cl.
USPC .......................................... 382/103; 348/169
(58) Field of Classification Search .................. 382/100, 382/103, 107, 181, 190, 195, 203; 348/135, 348/143, 169–172; 701/400
See application file for complete search history.

(56) References Cited

U.S. PATENT DOCUMENTS

| | | | | |
|---|---|---|---|---|
| 5,293,427 | A * | 3/1994 | Ueno et al. | 382/103 |
| 5,729,619 | A * | 3/1998 | Puma | 382/115 |
| 5,878,156 | A * | 3/1999 | Okumura | 382/118 |
| 6,717,518 | B1 * | 4/2004 | Pirim et al. | 340/576 |
| 7,821,409 | B2 * | 10/2010 | Ishida | 340/576 |
| 7,948,387 | B2 * | 5/2011 | Ishida et al. | 340/575 |
| 2006/0210165 | A1 | 9/2006 | Takemoto et al. | |
| 2008/0218359 | A1 | 9/2008 | Ishida et al. | |
| 2010/0202658 | A1 * | 8/2010 | Ishida et al. | 382/103 |

FOREIGN PATENT DOCUMENTS

| | | |
|---|---|---|
| JP | A-H05-060515 | 3/1993 |
| JP | A-H09-270010 | 10/1997 |
| JP | A-2001-167283 | 6/2001 |
| JP | A-2006-262010 | 9/2006 |
| JP | A-2007-151798 | 6/2007 |

OTHER PUBLICATIONS

Office Action mailed Dec. 21, 2010 issued in corresponding JP patent application No. 2009-027186 (English translation enclosed).

* cited by examiner

*Primary Examiner* — Anand Bhatnagar
(74) *Attorney, Agent, or Firm* — Posz Law Group, PLC

(57) ABSTRACT

A drowsiness detector detects the drowsiness by measuring a distance of an eyebrow at three points from a reference line defined by an inner eye corner and an outer eye corner. The three distances of the eyebrow from the reference line are respectively standardized by an inter-eye distance between the inner eye corners of the left and right eyes, and are respectively compared with thresholds for determining the rise of the eyebrow. The rise of the eyebrow is then translated as the start of the drowsiness, and is associated with an operation such as a doze prevention operation or the like.

14 Claims, 13 Drawing Sheets

FIG. 5
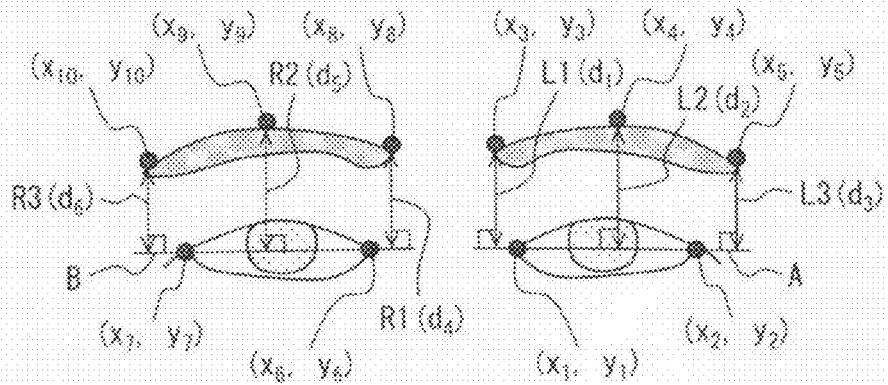
FIG. 7
| | $F_0$ | $F_1$ | $F_2$ | $F_3$ | ... | $F_{n-2}$ | $F_{n-1}$ | $F_n$ |
|---|---|---|---|---|---|---|---|---|
| (a) | 1 | 0 | 0 | 1 | ... | 0 | 1 | 1 |
| | $F_0$ | $F_1$ | $F_2$ | $F_3$ | ... | $F_{n-2}$ | $F_{n-1}$ | $F_n$ |
|---|---|---|---|---|---|---|---|---|
| (b) | 0 | 0 | 1 | 0 | ... | 1 | 1 | 0 |
FIG. 8
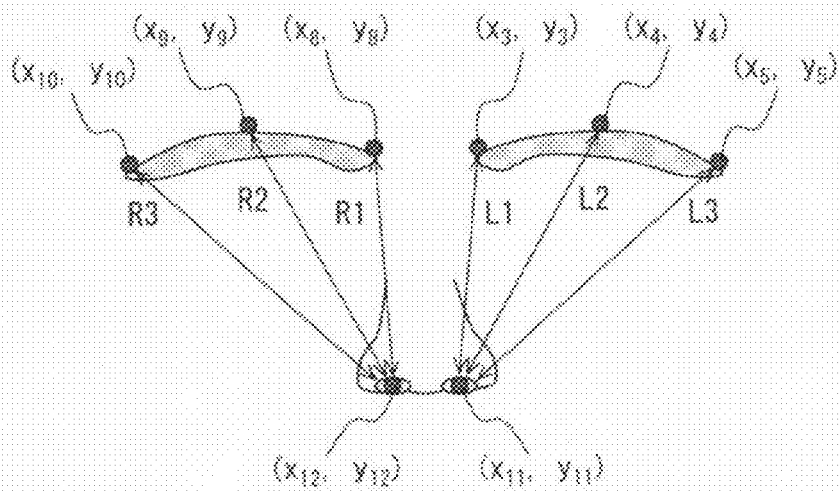

DROWSINESS DETECTOR

CROSS REFERENCE TO RELATED APPLICATION

The present application is based on and claims the benefit of priority of Japanese Patent Application No. 2009-27186, filed on Feb. 9, 2009, the disclosure of which is incorporated herein by reference.

FIELD OF THE INVENTION

The present disclosure generally relates to a drowsiness detection apparatus, a method of drowsiness detection, and a program for drowsiness detection.

BACKGROUND INFORMATION

Conventionally, drowsiness detection by various methods is proposed, for the purpose of preventing the drowsy driving of the vehicle. For example, the driver's face is captured by a camera in the vehicle, and the facial image of the driver is processed for detecting the drowsiness. Such an apparatus is disclosed in, for example, a Japanese patent document JP-A-2008-220424 (also available as a US patent document 20080218359).

The apparatus in the above document determines the eye opening degree and the eyebrow rising. By detecting the eye opening degree, the drowsiness can be detected, because the eye gradually closes as the drowsiness increases. Further, if the driver is in a situation such that he/she is currently driving a vehicle, the driver needs to resist the drowsiness, and thus struggles with the drowsiness by raising the eyebrow in an attempt to overcome the drowsiness. Therefore, by detecting the eyebrow rising, the drowsiness can also be detected.

The eyebrow rising for resisting the drowsiness is different person to person. That is, some people raise only the inner corners of the eyebrows, while other people raise only the outer corners of the eyebrows. Therefore, the rise of the eyebrow cannot be accurately detected, if only the center point of the eyebrow is measured for detecting the drowsiness of the driver who raises inner/outer eyebrow corners only.

In other words, the eyebrow rising detected only by the single point cannot yield an accurate detection result depending on the detection subject, thereby leading to a false detection of drowsiness.

SUMMARY OF THE INVENTION

In view of the above and other problems, the present disclosure provides an apparatus for accurate drowsiness detection, an accurate drowsiness detection method, and an accurate drowsiness detection' program.

In an aspect of the present disclosure, the drowsiness detector includes: an eyebrow positioning unit for determining a position of each of at least two horizontally-separate measurement points set on at least one of right and left eyebrows; and a detection unit for detecting drowsiness based on a vertical movement of the measurement points.

The drowsiness detector having the above construction can detect the eyebrow movement in a vertical direction at least two measurement points. Therefore, the vertical movement of the eyebrow of the subject of detection resisting the drowsiness can be accurately detected. In other words, the drowsiness detection can be accurately performed.

BRIEF DESCRIPTION OF THE DRAWINGS

Objects, features, and advantages of the present disclosure will become more apparent from the following detailed description made with reference to the accompanying drawings, in which:

FIG. 5 is an illustration of an eyebrow raise measurement method;

FIG. 7 is an illustration of history flags;

FIG. 8 is an illustration of an eyebrow rise measurement method in a second embodiment;

DETAILED DESCRIPTION (First Embodiment)

Figure 1:
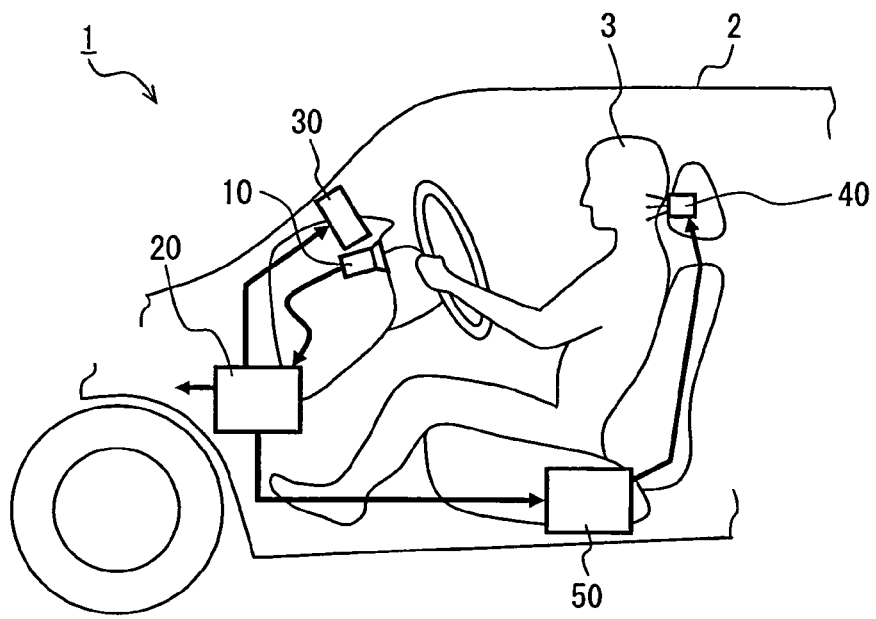
FIG. 1 is a schematic diagram of a doze prevention system in a first embodiment.

A doze prevention system 1 according to a first embodiment is mounted on a vehicle 2. As shown in FIG. 1, the doze prevention system 1 includes an imaging apparatus 10, a drowsiness determination apparatus 20, and other apparatuses. The imaging apparatus 10 is positioned so as to face the driver 3 in front of the driver 3 in the vehicle 2 and is constructed to capture a front facial image of the driver 3. The drowsiness determination apparatus 20 determines a drowsiness level based on the captured facial image. The other apparatuses include an alarm apparatus 30, a neck air conditioning actuator 40, and an aroma generation apparatus 50 that perform operations in accordance with determined drowsiness levels for attempting to bring an end a detected drowsy driving incident and restore the driver 3 to wakefulness.

Figure 2:
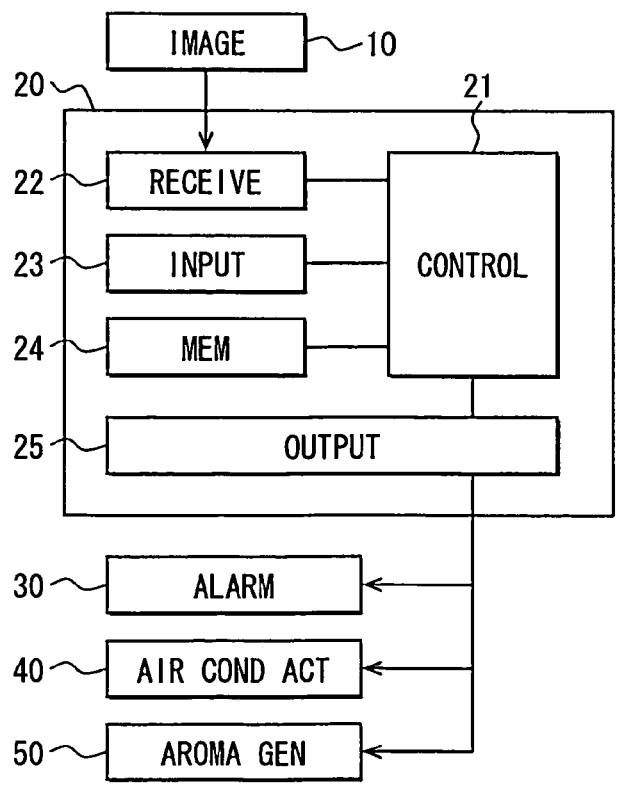
FIG. 2 is a block diagram of a drowsiness determination apparatus.

As shown in FIG. 2, the drowsiness determination apparatus 20 includes a control unit 21, a receiver unit 22, an input unit 23, a memory unit 24, and an output unit 25.

The control unit 21 of the drowsiness determination apparatus 20 controls the entire drowsiness determination apparatus 20 in accordance with a program stored in the memory unit 24.

Image data indicates a facial image captured by the imaging apparatus 10 and can be referred to herein as facial image data. The control unit 21 receives the facial image data from the receiver unit 22 and stores the facial image data in internal memory, which can be referred to as built-in memory, in real time. Based on the facial image data, the control unit 21 thereafter performs a wakefulness data collection process and a drowsiness detection process to be described in greater detail hereinafter.

The input unit 23 includes various buttons to receive inputs from the driver 3, and the inputs such as a start input that starts the wakefulness data collection process for collecting eyebrow position information of the driver 3 at his/her wakeful time are received therethrough.

The storage unit 24 includes areas for storing data such as a program for controlling the control unit 21 and various data and various flags to be described in greater detail hereinafter.

Based on the drowsiness detected by the control unit 21, the output unit 25 allows the alarm apparatus 30, the neck air conditioning apparatus 40, and the aroma generation apparatus 50 to perform doze preventing operations also to be described in greater detail hereinafter.

The alarm apparatus 30 has a display and a speaker, and can warn the driver 3 against the drowsy driving by outputting the warning information to the display and audibly outputting a warning to the speaker, such as a warning associated with the content of the display. For example, the warning information can include a message such as "Take a rest as soon as possible," and "Stop driving," or the like.

The neck air conditioning apparatus 40 is provided, for example, in a head rest of the seat for the driver 3 to send air to the neck of the driver 3 when the control unit 21 detects the drowsiness of the driver 3.

The aroma generation apparatus 50 generates an aroma having awakening effects and diffuses the aroma into the vehicle compartment when the control unit 21 detects the drowsiness of the driver 3.

At the time of drowsiness detection, other apparatuses and operations such as a seat belt winder for winding up the seat belt for awaking the driver from drowsiness, an automatic braking operation or the like may also be employed.

Various processes can be carried out by the control unit 21 of the doze prevention system 1 in the present embodiment are explained hereinafter.

For example, with reference to FIG. 4, a wakefulness data collection process can be performed by the control unit 21. When the start button of the input unit 23 is pressed, the wakefulness data collection process starts and collects the eyebrow position information at the wakeful time.

First, a variable i is set to 1 by the wakeful data collection process at S1.

Figure 4A:
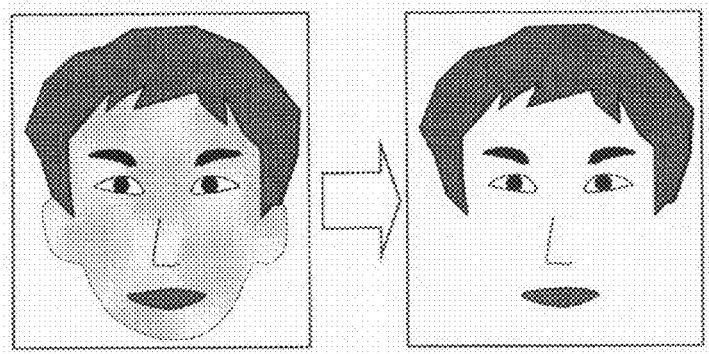
FIGS. 4A and 4B are illustrations of a position detection process.

The control unit 21 then detects position information based on the facial image data indicating the facial image captured by the imaging apparatus 10 at S2. The position information indicates positions of the eye and the eyebrow as well as nasal cavities in facial image data. The control unit 21 allows the imaging apparatus 10 to capture the facial image of the driver 3. Based on the facial image data indicating the facial image, the control unit 21 performs a binarization process for separating the facial image data into black and white portions as shown in FIG. 4A. Specifically, the technology disclosed in JP-A-H03-220633, for example, can be used for such separation.

Figure 4B:
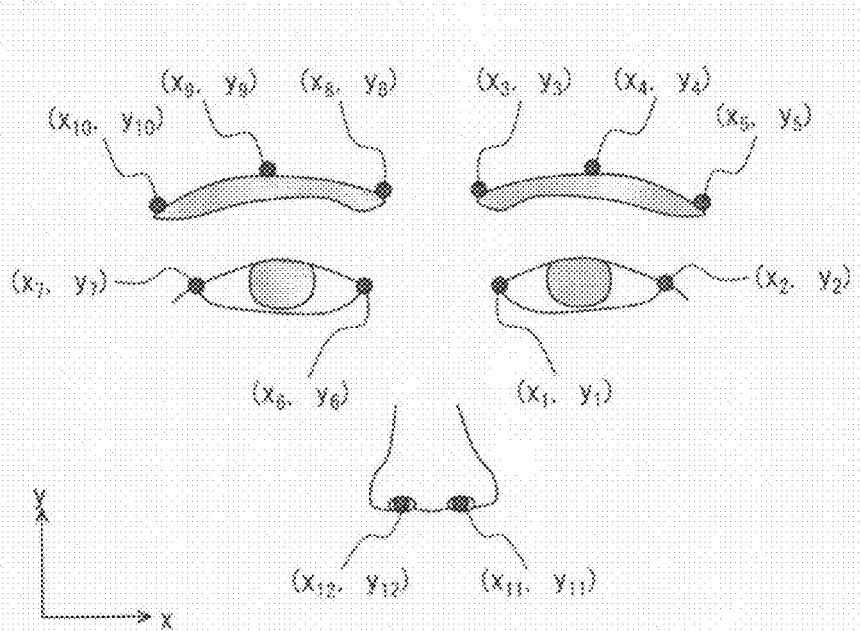

As shown in FIG. 4B, the control unit 21 detects positions of various features such as an inner corner of the left eye $(x_1, y_1)$, an outer corner of the left eye $(x_2, y_2)$, an inner corner of the left eyebrow $(x_3, y_3)$, a center of the left eyebrow $(x_4, y_4)$, an outer corner of the left eyebrow $(x_5, y_5)$, an inner corner of the right eye $(x_6, y_6)$, an outer corner of the right eye $(x_7, y_7)$, an inner corner of the right eyebrow $(x_8, y_8)$, a center of the right eyebrow $(x_9, y_9)$, an outer corner of the right eyebrow $(x_{10}, y_{10})$, a left nasal cavity $(x_{11}, y_{11})$, and a right nasal cavity $(x_{12}, y_{12})$. The feature positions of the eye are represented in (x, y) coordinates when the image from the above-mentioned image data is represented in an x-y plane. Specifically, the technology disclosed in JP-A-1996-101904 can be used. In this case, the center of the left eyebrow is positioned as a center point of the inner and outer corners of the left eyebrow in terms of a right-left direction of the eye. Likewise, the center of the right eyebrow is also positioned as a center point of the inner and outer corners of the right eyebrow.

Based on a detection result at S2, numerical values L1 to L3 and numerical values R1 to R3 showing the rise condition of the eyebrows (see FIG. 5) are calculated next at S3.

The above value L1 is calculated by an equation in the following, when a straight line A is defined as a line between the inner corner of the left eye $(x_1, y_1)$ and the outer corner of the left eye $(x_2, y_2)$ and a distance $d_1$ is defined as a distance from the inner corner of the left eyebrow $(x_3, y_3)$ to the line A in the facial image.

$$L1 = d_1 / \{(x_1-x_6)^2 + (y_1-y_6)^2\}^{0.5}$$

In the above equation, a portion of the equation $\{(x_1-x_6)^2+(y_1-y_6)^2\}^{0.5}$ represents a distance between the inner corner of the left eye and the inner corner of the right eye. Generally, any facial expression change causes only a small change in the distance between inner corners of the left and right eyes. A value relative to the distance between inner corners of the left and right eyes can be acquired by dividing the distance $d_1$ into the distance between the inner corners of the left and right eyes.

By using a ratio between distances as described, the problem associated with a change in the distance between the imaging apparatus 10 and the head of the driver 3 can be solved. As will be appreciated, such a change in the camera-subject distance changes the apparent distance in the facial image. For the same reason, the values of L2 to R3, to be described in greater detail hereinafter, are calculated based on a distance between the inner corners of the left and right eyes.

Further, the value L2 is calculated in the equation in the following, when a distance $d_2$ is defined as a distance between the line A and the center of the left eyebrow $(x_4, y_4)$ in the facial image.

$$L2 = d_2 / \{(x_1-x_6)^2 + (y_1-y_6)^2\}^{0.5}$$

Further, the value L3 is calculated in the equation in the following, when a distance $d_3$ is defined as a distance between the line A and the outer corner of the left eyebrow $(x_5, y_5)$ in the facial image.

$$L3 = d_3 / \{(x_1-x_6)^2 + (y_1-y_6)^2\}^{0.5}$$

Further, the value R1 is calculated by equation in the following, when a straight line B is defined as a line between the inner corner of the right eye $(x_6, y_6)$ and the outer corner of the right eye $(x_7, y_7)$ and a distance $d_4$ is defined as a distance from the inner corner of the right eyebrow $(x_8, y_8)$ to the line B in the facial image.

$$R1 = d_4 \{(x_1-x_6)^2 + (y_1-y_6)^2\}^{0.5}$$

Further, the value R2 is calculated in the equation in the following, when a distance $d_5$ is defined as a distance between the line B and the center of the right eyebrow $(x_9, y_9)$ in the facial image.

$$R2 = d_5 / \{(x_1-x_6)^2 + (y_1-y_6)^2\}^{0.5}$$

Further, the value R3 is calculated in the equation in the following, when a distance $d_6$ is defined as a distance between the line B and the outer corner of the right eyebrow ($x_{10}$, $y_{10}$) in the facial image.

$$R3=d_6/\{(x_1-x_6)^2+(y_1-y_6)^2\}^{0.5}$$

Then, each of the calculated values L1 to L3 and R1 to R3 is stored in the memory unit 24.

Then, the variable i is incremented to i+1 at S4. When the variable i is less than or equal to a specified value m, corresponding to YES at S5, the process returns to S2. When the variable i is not less than or equal to the specified value m, corresponding to NO at S5, the process terminates, and the memory unit 24 stores m counts of each of the values L1 to L3 and the values R1 to R3.

The control unit 21 calculates L1a to L3a and R1a to R3a at. S6, which are used as the thresholds for the rise of the eyebrow in the drowsiness detection process to be described in greater details hereinafter.

That is, the control unit 21 first reads all of m counts of L1 values stored in the memory unit 24. Then, based on the frequency distribution of all of the L1 values, the value L1a is defined as a boundary value of 5% range from the maximum of the cumulative relative frequency in the frequency distribution of L1 values. Then, other values L2a to R3a are defined in the same manner, based on the L2, L3, and R1 to R3. The defined values L1a to L3a and R1a to R3a are stored in the memory unit 24, and all of the stored values L1 to L3 and R1 to R3 in the memory unit 24 are deleted therefrom.

Then, the drowsiness detection process is started next at S7, and terminates the wakefulness data collection process.

Figure 6:
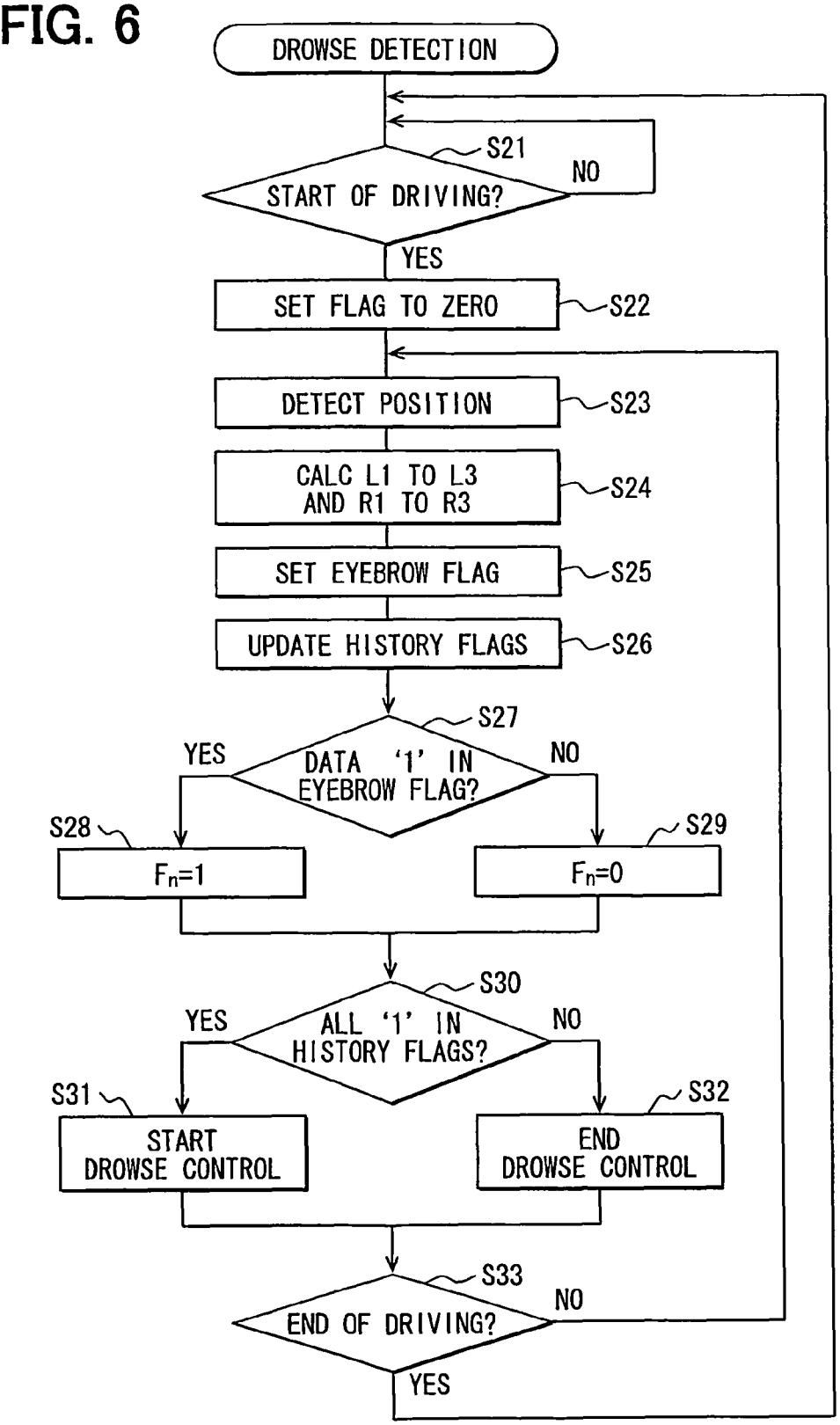
FIG. 6 is a flow diagram of a drowsiness detection process.

With reference to FIG. 6, the drowsiness detection process by the control unit 21 is explained. The drowsiness detection process is started at S7 of the wakefulness data collection process.

First, the process determines if the driver 3 has started driving the vehicle at S21.

When the driving of the vehicle is started, eyebrow rise flags (L1f, L2f, L3f, R1f, R2f, R3f) and history flags (F0-Fn) are all set to "0" at S22.

Then, position information is detected next at S23, and the values L1 to L3 and R1 to R3 are calculated based on the detected position information at S24. The position detection and calculation of the values L1 to L3 and R1 to R3 are performed in the same manner as S2 and S3 in FIG. 3.

Then, eyebrow rise flag setting is performed next at S25. That is, L1a calculated in S6 is compared with L1 calculated in S24, and L1f is set to "1" if L1 is greater than L1a. L1f is set to "0" if L1 is not greater than L1a. The other flags L2f, L3f and R1f to R3f are set in the same manner. That is, after comparing L2, L3, R1 to R3 calculated at S24 with the thresholds calculated at S6 of FIG. 3, values exceeding the threshold are flagged by the flag value of "1," and values not exceeding the threshold are flagged by the flag value of "0."

Then, history flags are updated next at S26. As shown in (a) portion of FIG. 7, the memory unit 24 stores n+1 counts of flags $F_0$ to $F_n$ in a table format. In that table, the flag information at each of positions $F_i$ (i=0, 1, 2 ... n−1, n) is slid to the flag information at the positions of $F_{n-1}$. In this case, the flag information in $F_0$ is deleted, and the flag information at $F_n$ is newly set to "0."

Then, whether there is an eyebrow rise flag having the value "1" is determined at S27. If at least one flag from among the flags L1f to L3f and R1f to R3f being set in S25 is set to "1," corresponding to YES at S27, $F_n$ is set to "1" at S28. If all of the flags L1f to L3f and R1f to R3f is set to "0," corresponding to NO at S27, $F_n$ is set to "0" at S29.

Then, whether all of the history flags $F_0$ to $F_n$ are set to "1" is determined at S30. That is, whether the history flags are set to "1" in succession for at least n+1 times is determined. By examining the history flag, the rise of the eyebrow is continued for at least a certain period is determined. The certain period of time is determined by the loop time of the process of S23 to S33 and the value of n. For example, if the process loops at every second and the value of n is 9, all of the flags $F_0$ to $F_n$ are set to "1" in ten seconds. That is, when the rise of the eyebrow continues for at least 10 seconds, all of the history flags $F_0$ to $F_n$ are set to "1." Therefore, the certain period of time mentioned above is defined by both of the loop time and the value of n.

If all the history flags $F_0$ to $F_n$ are set to "1," or eyebrow rise is continuing for a certain period, corresponding to YES at S30, the drowsiness is detected and a drowsiness control process is started at S31. More practically, an operation signal for operating the alarm apparatus 30, the neck air conditioning actuator 40, and/or the aroma generator 50 is output from the output unit 25. If the drowsiness control process has already been started, the drowsiness control process is continued.

If any one of the history flags is set to "0," corresponding to NO at S30, the drowsiness control process is terminated at S32.

Then, the process determines if the driver 3 has terminated driving the vehicle at S33. More practically, if the gear is put in a parking position, or if the ignition key is turned to an accessory (i.e., ACC) position with the engine of the vehicle being stopped, it is determined as the end of driving. If the end of the driving is determined, corresponding to YES at S33, the process returns to S21. If the end of the driving is not determined, corresponding to NO at S33, the process returns to S23.

The doze prevention system 1 configured in the above-described manner measures the eyebrow position at three points, that is, at the inner and outer corners of the eyebrow and the center of the two corners, thereby enabling an accurate detection of the rise of the eyebrow of the driver 3 when he/she struggles with the drowsiness. In addition, apparatuses for controlling the drowsiness can be operated based on the drowsiness detection, thereby effectively preventing the accidents due to the drowsy driving.

In addition, because the rise of the eyebrow at the time of measurement is detected based on the comparison of the eyebrow position to that of the wakeful time, the rise of the eyebrow due to the struggle with the drowsiness can be accurately detected.

Furthermore, the rise of the eyebrow is detected based on the distance from the reference line defined by the inner and outer corners of the eye. The eyebrow distance from the reference line is not substantially be affected by the change of the facial expression of the driver 3, thereby enabling a solid and accurate measurement of the eyebrow position at each of the measurement points.

Furthermore, because the rise of the eyebrow is determined by processing the image data from the imaging apparatus 10 disposed in the vehicle 2, there is no need to attach an eyebrow positioning apparatus on the face of the driver 3. That is, the rise of the eyebrow can be easily and readily detected by using the drowsiness determination apparatus 20 of the present invention.

(Second Embodiment)

The doze prevention system 1 in a second embodiment has basically the same configuration as the first embodiment and performs determination using the same determination principle as the first embodiment. However, some processes of the control unit 21 are changed and will be described below.

Various processes performed by the drowsiness determination apparatus 20 of the doze prevention system 1 according to the second embodiment will be described.

Figure 3:
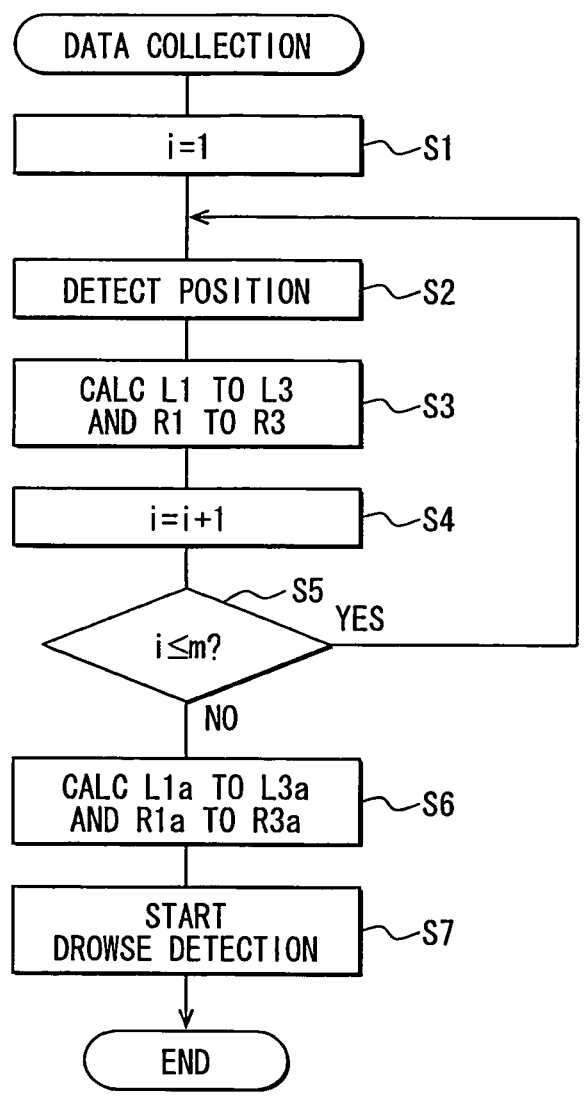
FIG. 3 is a flow diagram of a data collection process.

Compared to the first embodiment, the second embodiment uses a partially different method of collecting wakefulness data from the method in the first embodiment shown in FIG. 3. The difference is regarding S3 of the data collection process.

In the second embodiment, the value L1 is calculated based on a distance between a left nasal cavity $(x_{11}, y_{11})$ and the inner corner of the left eyebrow $(x_3, y_3)$ in the facial image as shown in FIG. 8. L1 is calculated by the following equation.

$$L1=\{(x_{11}-x_3)^2+(y_{11}-y_3)^2\}^{0.5}/\{(x_1-x_6)^2+(y_1-y_6)^2\}^{0.5}$$

A portion of the above equation, that is, $\{(x_1-x_6)^2+(y_1-y_6)^2\}^{0.5}$ is a distance between the inner corners of the right and left eyes. The standardization by this distance enables the change of the camera-subject distance less affecting to the measurement in the facial image.

The value L2 is calculated based on a distance between the left nasal cavity $(x_{11}, y_{11})$ and the center of the left eyebrow $(x_4, y_4)$ in the facial image. L2 is calculated by the following equation.

$$L2=\{(x_{11}-x_4)^2+(y_{11}-y_4)^2\}^{0.5}/\{(x_1-x_6)^2+(y_1-y_6)^2\}^{0.5}$$

The value L3 is calculated based on a distance between the left nasal cavity $(x_{11}, y_{11})$ and the outer corner of the left eyebrow $(x_5, y_5)$ in the facial image. L3 is calculated by the following equation.

$$L3=\{(x_{11}-x_5)^2+(y_{11}-y_5)^2\}^{0.5}/\{(x_1-x_6)^2+(y_1-y_6)^2\}^{0.5}$$

The value R1 is calculated based on a distance between a right nasal cavity $(x_{12}, y_{12})$ and the inner corner of the right eyebrow $(x_8, y_5)$ in the facial image. R1 is calculated by the following equation.

$$R1=\{(x_{12}-x_8)^2+(y_{12}-y_8)^2\}^{0.5}/\{(x_1-x_6)^2+(y_1-y_6)^2\}^{0.5}$$

The value R2 is calculated based on a distance between the right nasal cavity $(x_{12}, y_{12})$ and the center of the right eyebrow $(x_9, y_9)$ in the facial image. R2 is calculated by the following equation.

$$R2=\{(x_{12}-x_9)^2+(y_{12}-y_9)^2\}^{0.5}/\{(x_1-x_6)^2+(y_1-y_6)^2\}^{0.5}$$

The value R3 is calculated based on a distance between the right nasal cavity $(x_{12}, y_{12})$ and the outer corner of the right eyebrow $(x_{10}, y_{10})$ in the facial image. R3 is calculated by the following equation.

$$R3=\{(x_{12}-x_{10})^2+(y_{12}-y_{10})^2\}^{0.5}/\{(x_1-x_6)^2+(y_1-y_6)^2\}^{0.5}$$

Then, each of the calculated values L1 to L3 and R1 to R3 is stored in the memory unit 24, and the process proceeds to S4.

The drowsiness detection process in the second embodiment is basically the same as the process shown in FIG. 6 in the first embodiment. Compared to the first embodiment, the second embodiment uses a partially different method of drowsiness detection. The difference is regarding S24 of the drowsiness detection process. That is, the process in S24 is identical to the change from S3 in the first embodiment as described above.

The doze prevention system 1 in the second embodiment is advantageous because of the eyebrow position measurement based on the position of the nasal cavities. That is, even when the driver wears sunglasses or the like, the eyebrow positions can be accurately determined without using the inner/outer corners of the eyes, thereby enabling the accurate drowsiness detection.

In addition, other positions such as inner/outer eye corners may be used as reference points for determining the rise of the eyebrow, instead of using the nasal cavity. Further, the inner corner of the eyebrow may be measured relative to the inner corner of the eye, and the outer corner of the eyebrow may be measured relative to the outer corner of the eye, for example. That is, the different reference point may be used for respectively different measurement points.

(Third Embodiment)

The doze prevention system 1 in a third embodiment is basically configured in the same manner as the first embodiment, and performs drowsiness determination using the same determination principle as the first embodiment. However, some processes of the control unit 21 are changed and will be described below.

Various processes performed by the drowsiness determination apparatus 20 of the doze prevention system 1 according to the third embodiment will be described. Compared to the first and second embodiments, the third embodiment uses a different method of detecting the rise of the eyebrow. That is, an area of a polygon defined by multiple points on the face of the driver 3 is calculated to detect the rise of the eyebrow.

Figure 9:
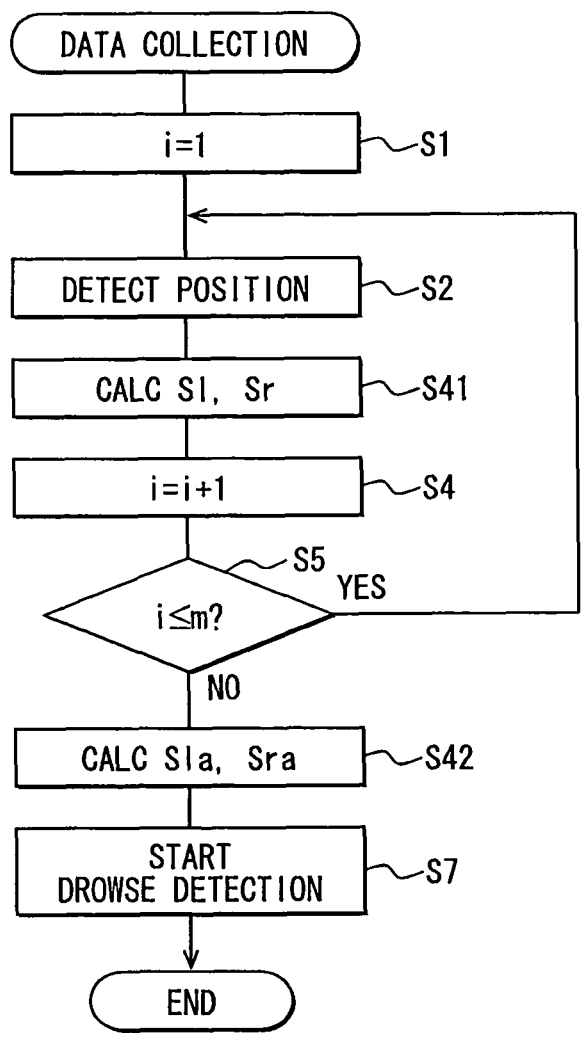
FIG. 9 is a flow diagram of a data collection process in a third embodiment.

The wakefulness data collection process in the third embodiment is explained with reference to FIG. 9.

In the present embodiment, the wakefulness data collection process performs the same process contents for S1, S2, S4, and S5 as the first embodiment, and performs different process contents for S3 and S6. That is, S3 is replaced with S41, and S6 is replaced with S42.

The change from S3 to S41 is the calculation of the values Sl and Sr based on the detection of the coordinates from the facial image in S2.

Figure 10:
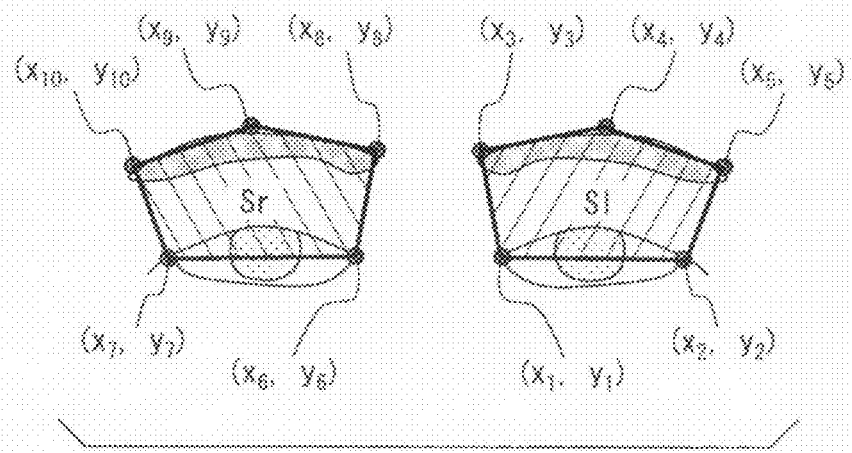
FIG. 10 is an illustration of an eyebrow raise measurement method.

That is, Sl is calculated based on an area value $S_1$ of a pentagon having five vertex points of inner corner of the left eye $(x_1, y_1)$, the outer corner of the left eye $(x_2, y_2)$, the inner corner of the left eyebrow $(x_3, y_3)$, the center of the left eyebrow $(x_4, y_4)$, and the outer corner of the left eyebrow $(x_5, y_5)$ as shown in FIG. 10. Sl is calculated by the following equation.

$$Sl=S_1/(x_1-x_6)^2+(y_1-y_6)^2$$

A portion of the above equation, $(x_1-x_6)^2+(y_1-y_6)^2$, is equal to an area of a square shape with a side of an inter inner-eye-corner distance between both eyes. That is, when the distance between the right and left eyes is measured by a distance between the inner corners of the right and left eyes, the square shape with a side of that inter-eye distance has the area size of $(x_1-x_6)^2+(y_1-y_6)^2$. The standardization of the $S_1$ by that inter-eye distance enables the camera-subject distance less affecting to the area of the pentagon in the facial image.

Sr is calculated based on an area value $S_2$ of a pentagon having five vertex points of inner corner of the right eye $(x_6, y_6)$, the outer corner of the right eye $(x_7, y_7)$, the inner corner of the right eyebrow $(x_6, y_8)$, the center of the right eyebrow $(x_9, y_9)$, and the outer corner of the right eyebrow $(x_{10}, y_{10})$ Sr is calculated by the following equation.

$$Sr=S_2/(x_1-x_6)^2+(y_1-y_6)^2$$

Then, Sl and Sr are stored in the memory unit 24, and the process proceeds to S4.

The change from S6 to S42 is that, when the variable i is not smaller than a certain value m (i.e., corresponding to NO in S5), the calculation of the threshold values Sla and Sra is performed for the detection of the rise of the eyebrow in the drowsiness detection process.

That is, the control unit 21 first reads all of m counts of Sl values stored in the memory unit 24. Then, based on the frequency distribution of all of the Sl values, the value Sla is calculated as a boundary value of 5% range from the maximum of the cumulative relative frequency in the frequency distribution of Sl values. Then, Sra is calculated in the same manner. Then, Sla and Sra are stored in the memory unit 24, and stored values Sl and Sr are all deleted from the memory unit 24. Then, the process proceeds to S7.

Figure 11:
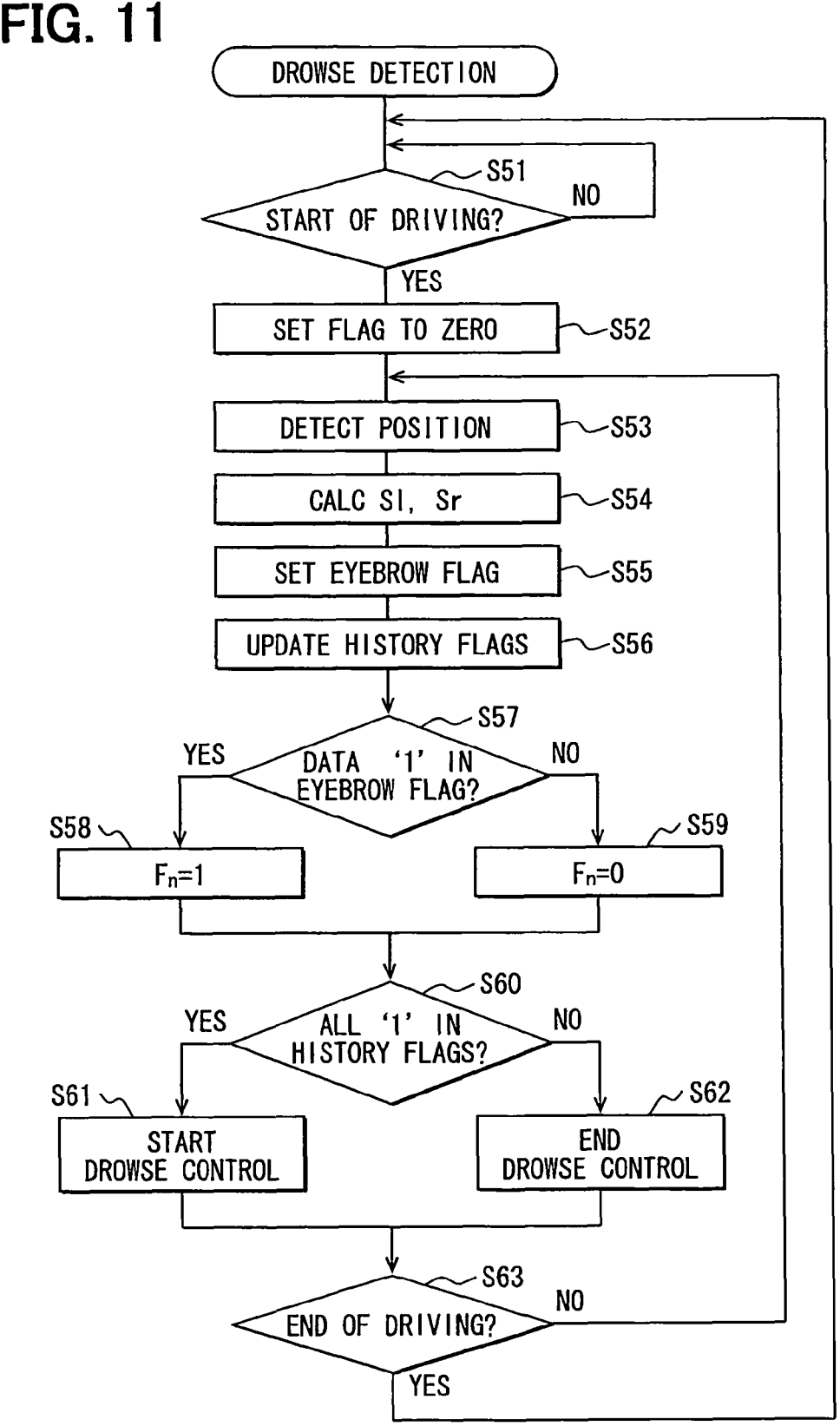
FIG. 11 is a flow diagram of a drowsiness detection process.

With reference to FIG. 11, the drowsiness detection process by the control unit 21 is explained. The drowsiness detection process is started at S7 of the wakefulness data collection process.

First, the process determines if the driver 3 has started driving the vehicle at S51.

When the driving of the vehicle is started, eyebrow rise flags (Lf, Rf) and history flags ($F_0$ to $F_n$) are all set to "0" at S52.

Then, position information is detected next at S53, and the values Sl and Sr are calculated based on the detected position information at S54. The position detection and calculation of the values Sl and Sr are performed in the same manner as S2 and S41 in FIG. 9.

Then, eyebrow rise flag setting is performed next at S55. That is, Sl calculated in S54 is compared with Sla calculated in S42 in FIG. 9, and Lf is set to "1" if Sl is greater than Sla. Lf is set to "0" if Si is not greater than Sla. The other flag Rf is set in the same manner. That is, Rf is set to "1" if Sr is greater than Sra, and Rf is set to "0" if Sr is not greater than Sra.

Then, the history flags are updated next at S56. The update of the history flags is performed in the same manner as S26 in FIG. 6.

Then, whether there is an eyebrow rise flag having the value "1" is determined at S57. The eyebrow rise flag $F_n$ is set to "1" at S58 if at least one of the flags Lf and Rf set in S55 is "1," which corresponds to YES at S57. Or, the eyebrow rise flag $F_n$ is set to "0" at S59 if all of the flags Lf and Rf set in S55 is "0," which corresponds to NO at S57.

Then, whether all of the history flags $F_0$ to $F_n$ are set to "1" is determined at S60. If all of the history flags $F_0$ to $F_n$ are set to "1," corresponding to YES at S60 showing that the rise of the eyebrow has been continued for a certain period of time, the drowsiness is detected and the drowsiness control process is started at S61. That is, the same process as S31 in FIG. 6 is started.

If any one of the history flags is set to "0," corresponding to NO at S60, the drowsiness control process is terminated at S62.

Then, the process determines if the driver 3 has terminated' driving the vehicle at S63. If the end of the driving is determined, corresponding to YES at S63, the process returns to S51. If the end of the driving is not determined, corresponding to NO at S63, the process returns to S53.

The doze prevention system 1 configured in the above-described manner detects the rise of the eyebrow by calculating an area of a pentagon defined by five points in the facial image. In addition, the object of area calculation may be different from the pentagonal shape. That is, instead of defining a pentagon, a four-sided shape may be defined by choosing one of the inner and outer corners of the eye with three eyebrow points. Or, a six-sided shape may be defined by adding the position of the nasal cavity to the pentagon.

(Fourth Embodiment)

The doze prevention system 1 in the fourth embodiment is basically the same as that of the first embodiment. However, some processes of the control unit 21 are changed and will be described below.

Figure 12:
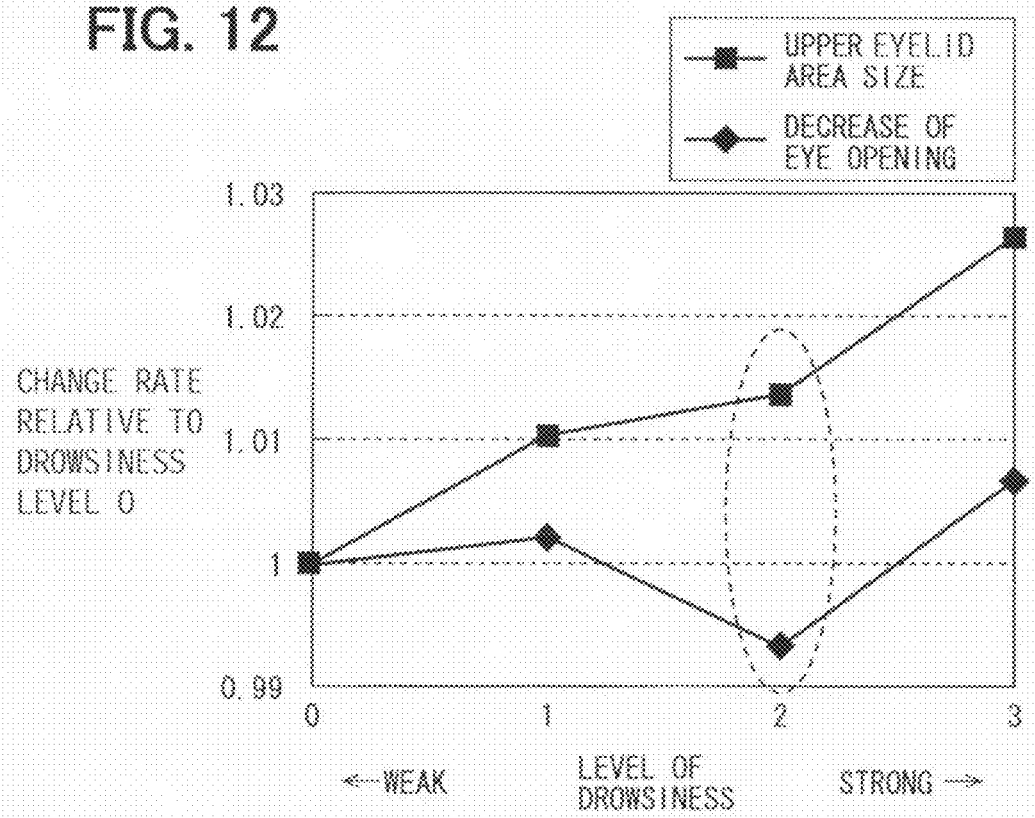
FIG. 12 is a graph of a relation between drowsiness levels, upper eyebrow area sizes and eye opening.

Various processes performed by the control unit 21 in the drowsiness determination apparatus 20 of the doze prevention system 1 according to the fourth embodiment will be described. In the fourth embodiment, an area of the upper eyelid is calculated for detecting the drowsiness. This is because of the erroneous drowsiness detection due to the defects in the conventional method. That is, in the conventional method, the eye opening degree is measured and the drowsiness is detected when the eye opening degree becomes smaller. However, according to the observation of testees, the eye opening degree is temporarily prevented from becoming smaller, or, in other words, the eye opening degree becomes greater, when the driver raises the eyebrow in a struggle with the drowsiness in an advanced drowsiness stage (See a dotted circle in FIG. 12, for example. Change rage of "decrease" of eye opening takes a value of less-than 1, which indicates an increase of the eye opening at drowsiness level 2.). As a result, the drowsiness of the driver is falsely overlooked in some cases by the conventional method that only detects the eye opening degree.

Therefore, in the present embodiment, the drowsiness detection process measures the area of the upper eyelid for detecting the drowsiness, because the upper eyelid area size increases substantially in proportion to the increase of drowsiness. In this case, the area of the upper eyelid is the area between the eyebrow and the upper edge of the eye.

Figure 13:
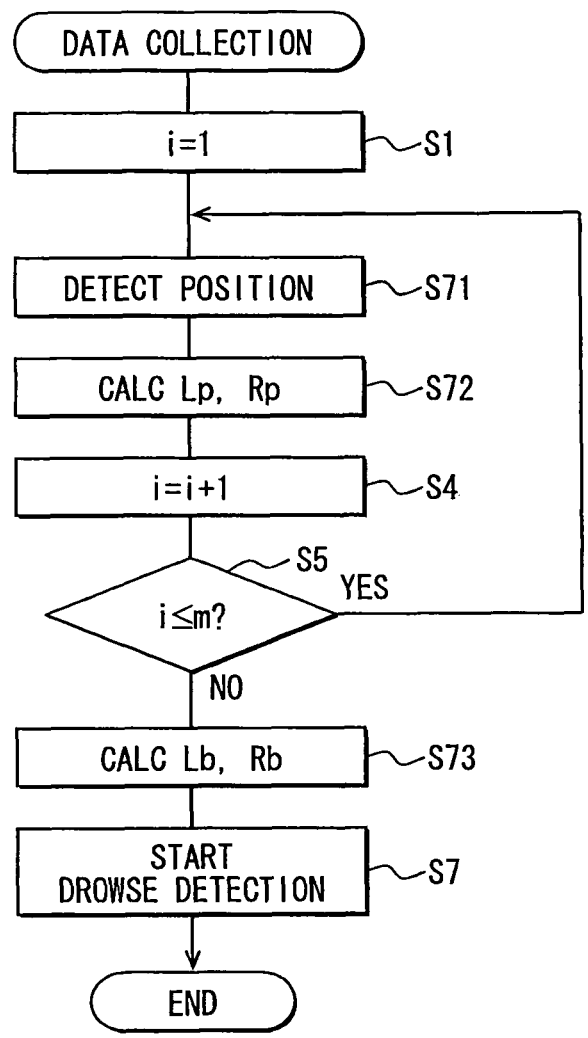
FIG. 13 is a flow diagram of a data collection process in a fourth embodiment.

The wakefulness data collection process in the fourth embodiment is explained with reference to FIG. 13.

In the present embodiment, the wakefulness data collection process performs the same process contents for S1, S4, S5 and S7 as the first embodiment, and performs different process contents for S2, S3 and S6. That is, S2 is replaced with S71, S3 is replaced with S72, and S6 is replaced with S73.

The S71 in place of S2 is explained in the first place. In S71, the position information indicating the position of the eye and the eyebrow is detected. More practically, the facial image from the imaging apparatus 10 is binarized to separate the black and white portions in the face of the driver 3 as shown in FIG. 4A.

Figure 14A:
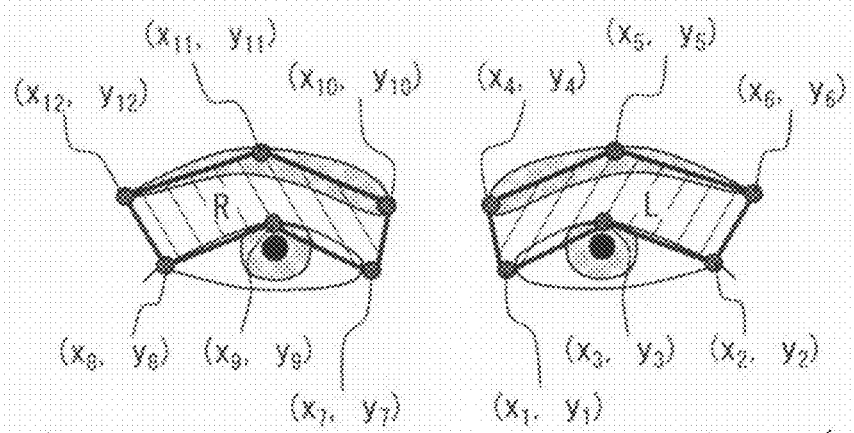
FIGS. 14A and 14B are illustrations of an area calculation method based on measurement points on the face.

Then, as shown in FIG. 14A, various feature positions are detected in the x-y plane of the facial image, such as an inner corner of the left eye ($x_1$, $y_1$), an outer corner of the left eye ($x_2$, $y_2$), a top of the left eye ($x_3$, $y_3$), an inner corner of the left eyebrow ($x_4$, $y_4$), a center of the left eyebrow ($x_5$, $y_5$), an outer corner of the left eyebrow ($x_6$, $y_6$), an inner corner of the right eye ($x_7$, $y_7$), an outer corner of the right eye ($x_8$, $y_8$), a top of the right eye ($x_9$, $y_9$), an inner corner of the right eyebrow ($x_{10}$, $y_{10}$), a center of the right eyebrow ($x_{11}$, $y_{11}$), and an outer corner of the right eyebrow ($x_{12}$, $y_{12}$).

In addition, in S71, Active Appearance Model (AAM) may be used to detect three dimensional position coordinates of each of the above points from the facial image captured by using only one camera.

Then, based on the detection result at S71, Lp and Rp are calculated next at S72. In this case, Lp and Rp are respectively derived from the six-sided shape of the upper eyelid. That is, as shown in FIG. 14A, Lp is calculated based on the six-sided shape defined by the inner corner of the left eye ($x_1$, $y_1$), the outer corner of the left eye ($x_2$, $y_2$), the top of the left eye ($x_3$, $y_3$), the inner corner of the left eyebrow ($x_4$, $y_4$), the center of the left eyebrow ($x_5$, $y_5$), and the outer corner of the left eyebrow ($x_6$, $y_6$), and Rp is calculated based on the six-sided shape defined by the inner corner of the right eye ($x_7$, $y_7$), the outer corner of the right eye ($x_8$, $y_8$), the top of the right eye ($x_9$, $y_9$), the inner corner of the right eyebrow ($x_{10}$, $y_{10}$), the center of the right eyebrow ($x_{11}$, $y_{11}$), and the outer corner of the right eyebrow ($x_{12}$, $y_{12}$). When the area of the six-sided shape is designated as $S_1$ and $S_2$, Lp and Rp are calculated by the following equations.

$$Lp = S_1/(x_1-x_7)^2+(y_1-y_7)^2$$

$$Rp = S_2/(x_1-x_7)^2+(y_1-y_7)^2$$

The areas $S_1$ and $S_2$ of the six-sided shape can be calculated by a well-known method. A portion of the above equations, that is, $(x_1-x_7)^2+(y_1-y_7)^2$ is equal to an area of a square shape with a side of an inter-eye distance between both eyes. The standardization of the $S_1$ and $S_2$ by the inter-eye distance enables the camera-subject distance less affecting to the area of the six-sided shape in the facial image. Then, Lp and Rp are stored in the memory unit 24, and the process proceeds to S4.

Figure 14B:
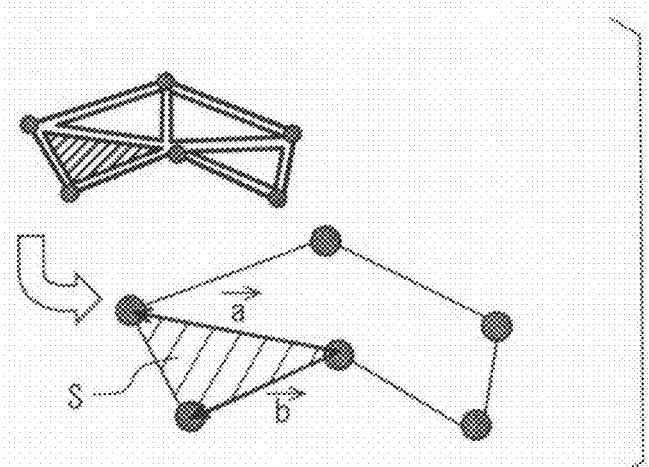

In this case, as shown in FIG. 14B, the six-sided shape may be divided into multiple triangles, and the area of each triangle may be calculated as an outer product of the relevant two vectors (e.g., $S = \vec{a} \times \vec{b}$), if feature points have been measured in the three dimensional coordinates at S71. The standardization of the area may also be performed by the inter-eye distance calculated in the three dimensional coordinates.

Then, S73 is performed if the variable i in S5 is not equal to or smaller than a certain value m, corresponding to NO in S5. That is, at S73, thresholds Lb and Rb for determining the rise of the eyebrow in the drowsiness detection process are calculated if a determination result in S5 is NO.

First, all of m counts of Lp are read from the memory unit 24. Then, based on the frequency distribution of all of the Lp values, the value Lb is calculated as a boundary value of 5% range from the maximum of the cumulative relative frequency in the frequency distribution of Lp values. The value Rb is calculated in the same manner. Then, Lb and Rb are stored in the memory unit 24, and stored values Lp and Rp are all deleted from the memory unit 24. Then, the process proceeds to S7.

Figure 15:
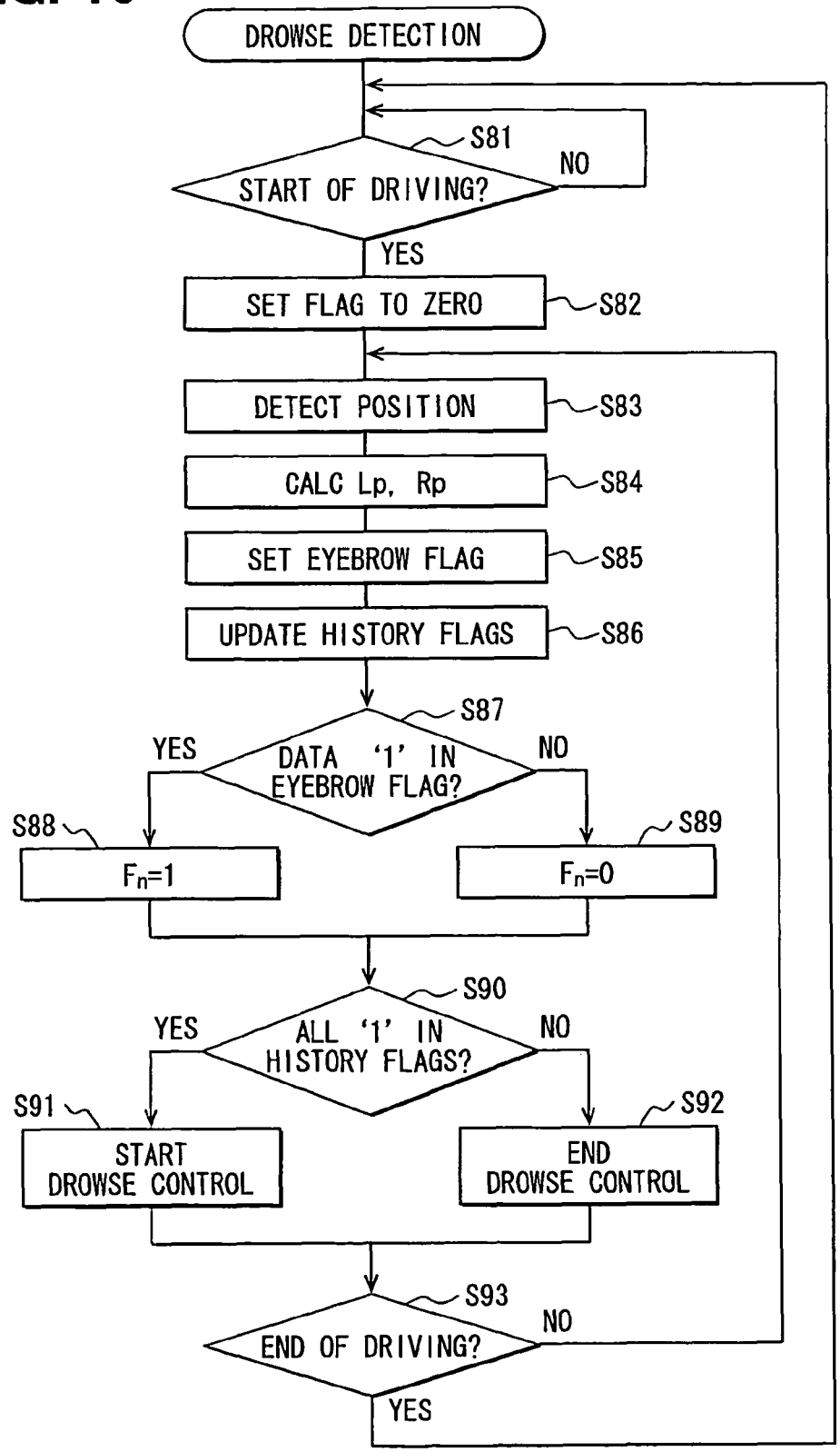
FIG. 15 is a flow diagram of a drowsiness detection process.

With reference to FIG. 15, the drowsiness detection process by the control unit 21 is explained. The drowsiness detection process is started at S7 of the wakefulness data collection process.

First, the process determines if the driver 3 has started driving the vehicle at S81.

When the driving of the vehicle is started, eyebrow rise flags (Lf, Rf) and history flags ($F_0$ to $F_n$) are all set to "0" at S82.

Then, position information is detected next at S83, and the values Lp and Rp are calculated based on the detected position information at S84. The position detection and calculation of the values Lp and Rp are performed in the same manner as S71 and S72 in FIG. 13.

Then, eyebrow rise flag setting is performed next at S85. That is, Lp calculated in S84 is compared with Lb calculated in S73 in FIG. 13, and Lf is set to "1" if Lp is greater than Lb. Lf is set to "0" if Lp is not greater than Lb. The other flag Rf is set in the same manner. That is, Rf is set to "1" if Rp is greater than Rb, and Rf is set to "0" if Rp is not greater than Rb.

Then, the history flags are updated next at S86. The update of the history flags is performed in the same manner as S26 in FIG. 6.

Then, whether there is an eyebrow rise flag having the value "1" is determined at S87. The eyebrow rise flag $F_n$ is set to "1" at S88 if at least one of the flags Lf and Rf set in S85 is "1," which corresponds to YES at S87. Or, the eyebrow rise flag $F_n$ is set to "0" at S89 if all of the flags Lf and Rf set in S85 are "0," which corresponds to NO at S87.

Then, whether all of the history flags $F_0$ to $F_n$ are set to "1" is determined at S90. If all of the history flags $F_0$ to $F_n$ are set to "1," corresponding to YES at S90 showing that the rise of the eyebrow has been continued for a certain period of time, the drowsiness is detected and the drowsiness control process is started at S91. That is, the same process as S31 in FIG. 6 is started.

If any one of the history flags $F_0$ to $F_n$ is set to "0," corresponding to NO at S90, the drowsiness control process is terminated at S92.

Then, the process determines if the driver 3 has terminated driving the vehicle at S93. If the end of the driving is determined, corresponding to YES at S93, the process returns to S81. If the end of the driving is not determined, corresponding to NO at S93, the process returns to S83.

The area of the upper eyelid increases when (a) degree of eye opening is decreased, or (b) the eyebrow is raised. In other words, the increase of the area of the upper eyelid is translated as at least one of the following two conditions: (a) the decrease of the eye opening degree, and (b) the rise of the eyebrow.

Therefore, the doze prevention system 1 configured in the above-described manner can highly accurately detect the drowsiness of the driver, because the rise of the eyebrow due to the increased drowsiness, in addition to the decrease of the eye opening degree at the start of drowsiness, can be more securely detected, in comparison to the drowsiness detection based only on measurement of the eye opening degree.

The conventional method of drowsiness detection based only on the measurement of the eye opening degree is not capable of accurately detecting the drowsiness, due to errors associated with the following problem. That is, at the time of eyebrow rising due to the increase of drowsiness, the eye opening degree may not decrease due to the raised eyebrow that pulls up the upper eyelid. In other words, the increase of drowsiness causes the increase of the eye opening degree, which results in the false detection of decrease of the drowsiness, if the drowsiness detection is based only on the eye opening degree. The doze prevention system 1 in the present invention is free from that problem, due to the well-sorted method described in the above embodiments.

The area of the upper eyelid may be measured in a different manner. That is, the top of the eye may be defined by two or more points on the edge of the eye, instead of only one point on the edge of the eye. In other words, the six-sided shape of the upper eyelid may be replaced with other shapes. That is, only the top point of the eye and eyebrow points may be used to define the measurement polygon without using the inner/outer eye corners.

Although the present disclosure has been fully described in connection with preferred embodiment thereof with reference to the accompanying drawings, it is to be noted that various changes and modifications will become apparent to those skilled in the art.

For example, the fall of the eyebrow may be additionally considered for detecting the drowsiness. That is, the fall of the eyebrow to the original eyebrow position due to the increase of the drowsiness may follow the rise of the eyebrow due to the struggle with the drowsiness, as already noted. The fall of the eyebrow after the eyebrow rising may thus be used as an indicator of more seriously increased drowsiness. Further, the eye opening degree and the eyebrow rising may be combined for detecting the degree of drowsiness.

Furthermore, the eyebrow positioning may use four or more points on the eyebrow, instead of using only three points at an inner/outer corner and a center of the eyebrow. That is, for example, evenly-spaced and laterally-arranged four or more points on the eyebrow may be used to detect the measurement of the eyebrow position.

Furthermore, the threshold of the eyebrow rising may be calculated based on t-test or other method, instead of the wakefulness data collection process.

Furthermore, the electromyogram of the facial muscles may be employed for detecting the eyebrow movement, instead of processing the facial image of the driver.

Furthermore, the drowsiness detection may be based on only one of the right and left eyebrows, instead of using both of the right and left eyebrows.

Such changes, modifications, and summarized schemes are to be understood as being within the scope of the present disclosure as defined by appended claims.

(Personal Difference of Eyebrow Rising Position)

The eyebrow rising position is different person to person. The personal difference of eyebrow rising position is confirmed by the following test.

(1) Summary

Figure 16:
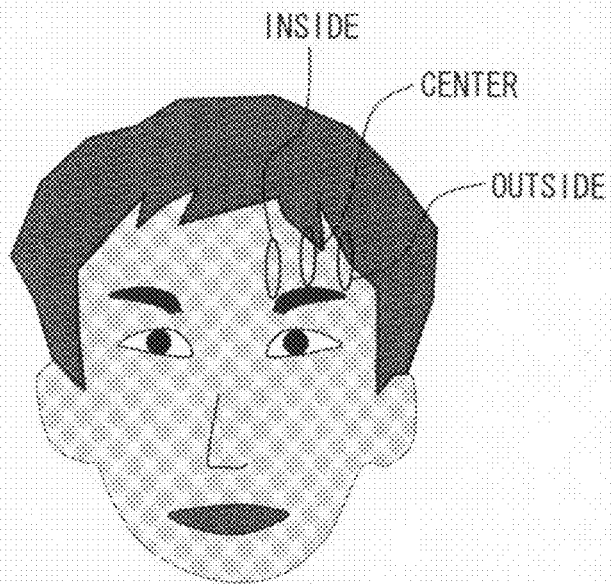
FIG. 16 is an illustration of muscle positions on the face.

Seven testees (males and females) are examined by a test that simulates a high speed driving through a simple operation task, for the purpose of drowsiness evaluation and myopotential measurement of frontalis muscles at three forehead positions (inside, center and outside, as shown in FIG. 16).

(2) Task

Figure 17:
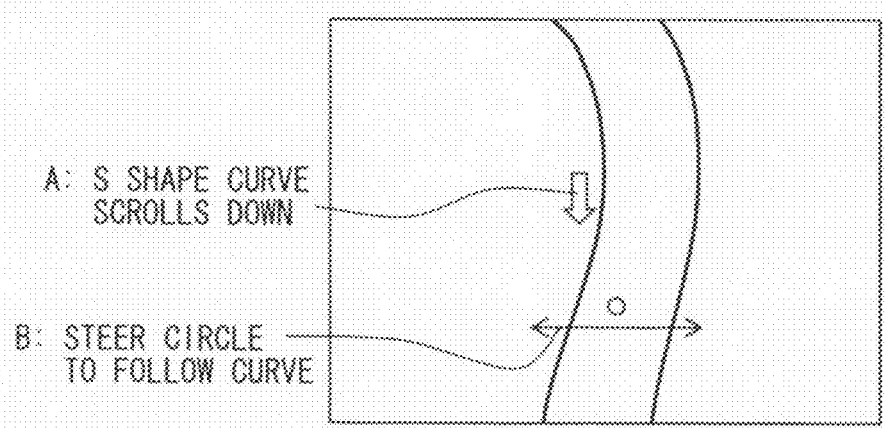
FIG. 17 is an illustration of a tracking task.

Testees are asked to trace the S shape curve by steering a circle. That is, the testee steers a small circle right and left between the two S shape curves as the curve scrolls down on the screen, which is illustrated in FIG. 17.

(3) Drowsiness evaluation

The facial expression of the testee at the time of performing the above task is compared with his/her facial expression of the wakeful time. The comparison is rated into six levels of 0 to 5 as described below for every five seconds. Five to seven examiners are employed to evaluate the testees.

The drowsiness is rated as increasing when the level number increases. That is, level 0 of the evaluation is for no drowsiness, level 1 is for only a little drowsiness, level 2 is for medium drowsiness, level 3 is for increased drowsiness, level 4 is for seriously increased drowsiness, and level 5 is for falling asleep.

More concrete and practical evaluation method is described in the following document.

Hiroki KITAJIMA and three others: Prediction of Automobile Driver Sleepiness: 1st Report, Rating of Sleepiness Based on Facial Expression and Examination of Effective Predictor Indexes of Sleepiness, Transactions of The Japan Society of Mechanical Engineers. C 63(613) pp. 3059-3066 19970925.

(4) Analysis and Conclusion

The myopotential at the drowsiness level of 3, at which level the driver struggles with the drowsiness, is measured and analyzed. That is, an RMS value is calculated for all samples of myopotential (for a 5 second period), and then the average of 10 samples is calculated. After sampling, the averaged RMS value is standardized by the RMS value of impassive time (at a time of no facial expression with wakefulness), for the purpose of removing the influence of personal difference as well as the influence of the electrode wear condition such as positions of the electrodes, resistance between the electrode and the skin, and the like.

The following equation is used for the standardization of RMS value.

Figure 18:
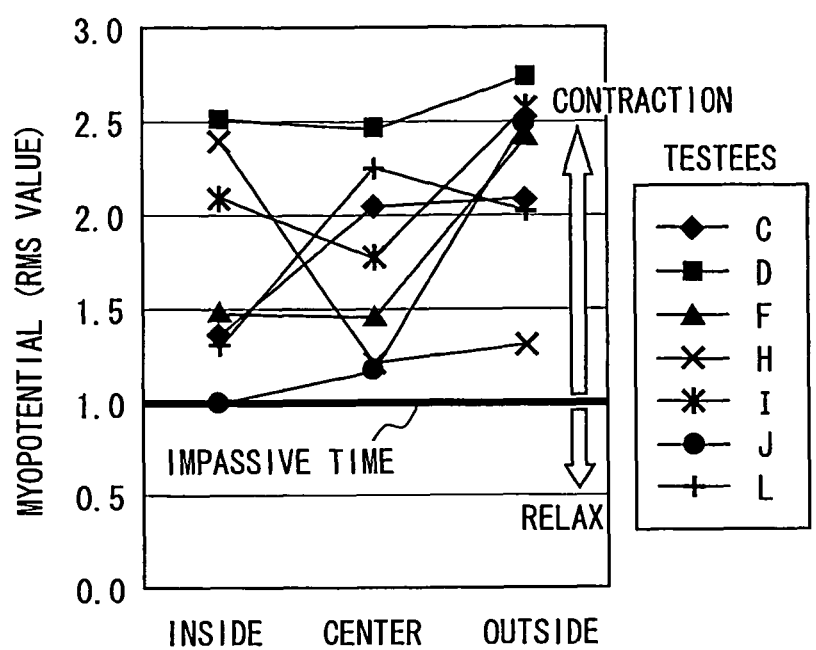
FIG. 18 is a graph of muscle activities at respective muscle positions.

Standardized RMS=the averaged RMS value at level 3/the RMS value of impassive time FIG. 18 shows a graph of frontalis muscle activity at the drowsiness level 3. In this graph, the vertical axis represents the standardized RMS value, and the horizontal axis represents the positions of the frontalis muscles. The standardized RMS value of 1.0 indicates that the frontalis muscles are neither contracted nor relaxed relative to the impassive time (at a time of no facial expression with wakefulness). In other words, the eyebrow position rests at the position of impassive time when the standardized RMS value is equal to 1.0. When the standardized RMS value increases to a greater value, the muscle is more contracted and the eyebrow is raised.

The graph shows that all of the seven testees have the frontalis muscles contracted at various positions, indicating that the eyebrows of respective testees are raised at variously different positions.

Therefore, the personal difference of the eyebrow rising among the seven testees is confirmed from the graph.

What is claimed is:

1. A drowsiness detector comprising:
   an eyebrow positioning unit for determining a position of each of at least two horizontally-separate measurement points set on at least one of right and left eyebrows, the at least two horizontally-separate measurement points being on the same one of right and left eyebrows; and
   a detection unit for detecting drowsiness based on a vertical movement of the measurement points, wherein the detection unit detects drowsiness when an upward movement of the measurement points is detected.

2. The drowsiness detector of claim 1, wherein
   the detection unit detects drowsiness based on the vertical movement of at least one of the measurement points.

3. The drowsiness detector of claim 1, wherein
   the detection unit compares the positions of the measurement points at a wakeful time with the positions of the respective measurement points at a drowsiness detection time for detecting the vertical movement of measurement points.

4. The drowsiness detector of claim 1, wherein
   three measurement points are set at an inner corner, an outer corner, and a substantial-center point of the eyebrow.

5. The drowsiness detector of claim 1, wherein
   the detection unit measures the vertical movement of the position of the measurement point relative to a static reference point or a static reference line.

6. The drowsiness detector of claim 5, wherein
   the static reference line is a straight line defined by an inner corner and an outer corner of an eye, and
   the static reference point is a position of at least one of the inner corner of the eye, the outer corner of the eye, and a nasal cavity.

7. The drowsiness detector of claim 6, wherein
   the eyebrow positioning unit measures the position of the measurement point based on image data of a face image, and
   the detection unit measures the position of at least one of the inner and outer eye corners and the nasal cavity.

8. The drowsiness detector of claim 1, wherein
   the detection unit detects the vertical movement of the position of at least one of the measurement points based on an area size of a polygon, and
   the polygon is defined by at least one of an inner and outer eye corners and a nasal cavity, together with at least two of the measurement points.

9. The drowsiness detector of claim 1, wherein
   the detection unit detects the vertical movement of the position of at least one of the measurement points based on an area size of a polygon, and the polygon is defined by an eye top point and a nasal cavity, together with at least two of the measurement points.

10. The drowsiness detector of claim 9, wherein
the eyebrow positioning unit measures the position of the measurement point based on image data of a face image, and
the detection unit measures the position of the eye top point based on image data of a face image.

11. The drowsiness detector of claim 1, wherein
the eyebrow positioning unit measures the position of the measurement point based on image data of a face image.

12. The drowsiness detector of claim 11 further comprising:
an image unit for generating the image data of the face image in a vehicle.

13. A non-transitory computer readable storage medium storing an instruction for causing a computer to provide the eyebrow positioning unit and the detection unit of claim 1.

14. A method of detecting drowsiness comprising steps of:
determining a position of each of at least two horizontally-separate measurement points that define at least one of right and left eyebrows, the at least two horizontally-separate measurement points being set on the same one of right and left eyebrows; and
detecting drowsiness based on an upward movement of the measurement points.

* * * * *